United States Patent [19]

Tamura et al.

[11] Patent Number: 5,702,882
[45] Date of Patent: *Dec. 30, 1997

[54] REAGENT FOR ENDOTOXIN-SPECIFIC ASSAY

[75] Inventors: Hiroshi Tamura; Toshio Oda; Shigenori Tanaka, all of Tokyo, Japan

[73] Assignee: Seikagaku Kogyo Kabushiki Kaisha (Seikagaku Corporation), Tokyo, Japan

[*] Notice: The portion of the term of this patent subsequent to Jan. 3, 2015, has been disclaimed.

[21] Appl. No.: 313,899

[22] Filed: Sep. 28, 1994

[30] Foreign Application Priority Data

Sep. 30, 1993 [JP] Japan .................... 5-265479

[51] Int. Cl.$^6$ .............. C12Q 1/00; C12Q 1/34; C12Q 1/56; G01N 33/53
[52] U.S. Cl. .............. 435/4; 435/18; 435/13; 435/23; 435/184; 435/975; 435/14; 436/74; 436/69; 436/63
[58] Field of Search .............. 435/4, 18, 13, 435/23, 184, 975; 436/63, 74, 69, 14

[56] References Cited

U.S. PATENT DOCUMENTS

| | | | |
|---|---|---|---|
| 4,322,217 | 3/1982 | Dikeman | 435/4 |
| 5,047,353 | 9/1991 | Tsuchiya et al. | 435/4 |
| 5,155,032 | 10/1992 | Tanaka et al. | 435/4 |
| 5,179,006 | 1/1993 | Matuura et la. | 435/4 |
| 5,286,625 | 2/1994 | Tanaka et al. | 435/4 |
| 5,378,610 | 1/1995 | Tanaka et al. | 435/18 |
| 5,389,547 | 2/1995 | Tanaka et al. | 435/4 |
| 5,401,647 | 3/1995 | Tanaka et al. | 435/4 |

FOREIGN PATENT DOCUMENTS

| | | |
|---|---|---|
| 0513361 | 11/1992 | European Pat. Off. . |
| 0522965 | 7/1993 | European Pat. Off. . |
| 0569033 | 11/1993 | European Pat. Off. . |
| 0588303 | 3/1994 | European Pat. Off. . |
| 0613004 | 8/1994 | European Pat. Off. . |
| 0507952 | 10/1994 | European Pat. Off. . |
| 2216462 | 8/1990 | Japan . |
| 2221863 | 9/1990 | Japan . |

*Primary Examiner*—Gary E. Hollinden
*Assistant Examiner*—Louise Leary
*Attorney, Agent, or Firm*—Sughrue, Mion, Zinn, Macpeak & Seas

[57] ABSTRACT

Endotoxin (Et) can be specifically assayed by exclusively utilizing the factor C system reaction without being affected by factor G contained in a limulus amebocyte lysate reagent.

The present invention provides: (1) a reagent for ET-specific assay which comprises a limulus amebocyte lysate reagent and an alkylglucoside; (2) a method of specifically assaying Et in a specimen using a limulus amebocyte lysate reagent, wherein an alkylglucoside is added to the limulus amebocyte lysate reagent and/or the specimen; and (3) a factor G activation inhibitor composition which comprises an alkylglucoside as an active ingredient capable of inhibiting the activation of factor G in limulus amebocyte by $(1\rightarrow3)$-$\beta$-D-glucan.

19 Claims, 2 Drawing Sheets

REAGENT FOR ENDOTOXIN-SPECIFIC ASSAY

FIELD OF THE INVENTION

This invention relates to a reagent for endotoxin-specific assay, a method for assaying endotoxin, a kit for use in the assay method, a factor G activation inhibitor composition each with the use of a limulus amebocyte lysate reagent.

BACKGROUND OF THE INVENTION

There has been known a method for assaying endotoxin (hereinafter sometimes referred to simply as Et) with the use of limulus amebocyte lysate (hereinafter sometimes referred to simply as lysate). This assay method is generally called "limulus test" and the reaction of the lysate participating in this assay is called "limulus reaction". Owing to the high detection sensitivity, this method has been frequently employed in various fields including pyrogen check of drugs or water and clinical diagnosis. This method is based on coagulation of the lysate in the presence of a trace amount of Et. The latest biochemical studies have clarified that this reaction consists of stepwise activation of several coagulation factors [J. Protein Chem., 5, 255–268 (1986)].

This reaction using a lysate obtained from *Tachypleus tridentatus* will be illustrated with reference to FIG. 1. When Et is added to the lysate, factor C (an Et-sensitive factor, molecular weight: 123,000) existing in the lysate is activated. Then the activated factor C thus formed limitedly hydrolyzes a specific site of factor B (molecular weight: 64,000) to thereby form activated factor B. The activated factor B activates proclotting enzyme (molecular weight: 54,000) to thereby convert into clotting enzyme. The clotting enzyme limitedly hydrolyzes coagulogen (coagulant protein, molecular weight: 19,723) at specific sites (i.e., $Arg^8$-$Thr^{19}$ and $Arg^{46}$-$Gly^{47}$) in a loop crosslinked with a disulfide bond. Thus a peptide C represented by H-$Thr^{19}$ ... $Arg^{46}$-OH (consisting of 28 amino acid residues) is liberated and the residual part is converted into a coagulin gel. Thus, the limulus reaction is composed of a series of reactions, which is also called a cascade reaction. (This cascade reaction triggered by Et will be hereinafter referred to as the factor C system reaction.)

On the other hand, it has been clarified that the lysate reacts not only to Et but also to (1→3)-β-D-glucan (hereinafter sometimes referred to simply as β-glucan) in the specimen. That is to say, factor G (a β-glucan sensitive factor) shown in FIG. 1 is activated and the activated factor G thus formed activates the proclotting enzyme into the clotting enzyme to thereby form a coagulin gel. (This cascade reaction triggered by β-glucan will be hereinafter referred to as the factor G system reaction.)

The clotting enzyme formed in the above cascade reactions hydrolyzes an amide bond in a synthetic substrate, which is separately added to the reaction system, for example, t-butoxycarbonyl-leucyl-glycyl-arginine-paranitroanilide (Boc-Leu-Gly-Arg-pNA), Boc-Val-Leu-Gly-Arg-pNA (SEQ ID NO: 1), benzyloxycarbonyl-leucyl-glycyl-arginine-paranitroanilide (Z-Leu-Gly-Arg-pNA), Boc-Ile-Glu-Gly-Arg-pNA (SEQ ID NO: 2), Boc-Val-Ser-Gly-Arg-pNA (SEQ ID NO: 3) or Boc-Ser-Gly-Arg-pNA, to thereby liberate paranitroaniline. Therefore, Et or β-glucan can be quantitative by measuring the absorbance of the chromogenic substance (paranitroaniline).

As discussed above, a lysate usually contains a component which participates in both of the factor C system reaction and the factor G system reaction. When Et in a specimen is to be assayed by using such a lysate, it is feared that the factor G system reaction would proceed by β-glucan which might be contained in the specimen and results in incorrect data.

Thus it has been proved that the limulus test is an assay method which is not specific for Et and, therefore, the attempts have been made to establish a method for Et-specific assay.

For example, it is known that when a polyglycoside having a definite number of (1→3)-β-D-glucoside structural units binding thereto is added to the lysate or an insoluble carrier on which the polyglycoside is immobilized or the polyglycoside which is water-insoluble is brought into contact with the lysate, the activation of factor G can be inhibited without affecting the factor C system reaction and thus endotoxin can be specifically assayed (U.S. Pat. Nos. 5,155,032, 5,179,006 and 5,047,353, JP-A-2-216462, JP-A-221863 and WO92/06381; the term "JP-A" as used herein means an "unexamined published Japanese patent application").

However, these method requires a complicated operation including partial decomposition and/or fractionation of the (1→3)-β-D-glucan, collection of a fraction inhibiting the activation of factor G and, further, removal of the endotoxin.

The known methods of pretreating a specimen to be subjected to the Et-specific assay include: 1) a method comprising treating whole blood with n-alkylglucoside and nitric acid (U.S. Pat. No. 5,286,625), 2) a method comprising treating plasma or serum with a mixed solution of a) n-alkylglucoside, b) a compound having an imidazolyl group or an amino group and c) alkaline earth metal salt and alkaline metal hydroxide (EP-A-0 513 361), 3) a method comprising mixing a specimen with a pretreating composition containing n-alkylglucoside, a hexadimethrine compound, an alkaline metal hydroxide and an alkaline earth metal halide and heating the resulting mixture (EP-A-0 569 033) and 4) a method comprising diluting a specimen with an aqueous solution of n-octyl-β-D-glucoside and heating the mixture at 60° to 100° C. for 3 to 20 minutes (EP-B-0 552 965).

These methods relates to pretreatment of a specimen to efficiently extract Et therefrom for Et assay, but the above-described references do not disclose the action and effect of inhibiting activation of factor G existing in the lysate.

Further, it has been known to use a reagent for Et assay comprising the lysate and a buffered dispersion of nonionic surfactant (Tween-80® and Tween-20®) (U.S. Pat. No. 4,322,217).

However, when Et in a specimen is assayed using the reagent, the factor G system reaction proceeds by β-glucan contaminating the specimen and therefore, a correct result cannot be obtained.

SUMMARY OF THE INVENTION

An objective of the present invention is to assay Et conveniently and specifically in a specimen using a limulus amebocyte lysate reagent in which the factor C system reaction alone proceeds without being affected by factor G (β-glucan-sensitive factor) existing in the lysate.

In order to achieve the above-mentioned objective, the present inventors have examined a substance selectively inhibiting the factor G system reaction, namely, the activation of factor G by β-glucan and/or the activity of the activated factor G without inhibiting the factor C system reaction in the lysate. As a result, it has been successfully found that when an alkylglucoside is added to the lysate, the factor G system reaction caused by β-glucan can be strongly inhibited while the factor C system reaction caused by Et cannot be substantially inhibited.

It has been further found that the above-mentioned objective can be easily achieved, in particular, by using an appropriate amount of an alkyl-β-D-glucoside which can be easily obtained as an nonionic surfactant.

Accordingly, the present invention provides: (1) a reagent for endotoxin-specific assay which comprises a limulus amebocyte lysate reagent and an alkylglucoside; (2) a reagent for endotoxin-specific assay as described in the above (1) wherein said alkylglucoside is an alkyl-O-β-D-glucoside or an alkyl-S-β-D-glucoside; and (3) a factor G activation inhibitor composition which comprises an alkylglucoside as an active ingredient capable of inhibiting activation of factor G by (1→3)-β-D-glucan in limulus amebocyte.

Further, the present invention provides a kit for Et-specific assay which contains a limulus amebocyte lysate reagent and an alkylglucoside as constituent reagents.

Furthermore, the present invention provides a method for Et-specific assay in a specimen using a limulus amebocyte lysate reagent, which comprises adding an alkylglucoside to the limulus amebocyte lysate reagent and/or the specimen.

Furthermore, the present invention provides a method for inhibiting activation of factor G which comprises adding alkylglucoside to a limulus amebocyte lysate reagent containing factor G which would be activated by β-glucan.

DETAILED DESCRIPTION OF THE INVENTION

Figure 1:
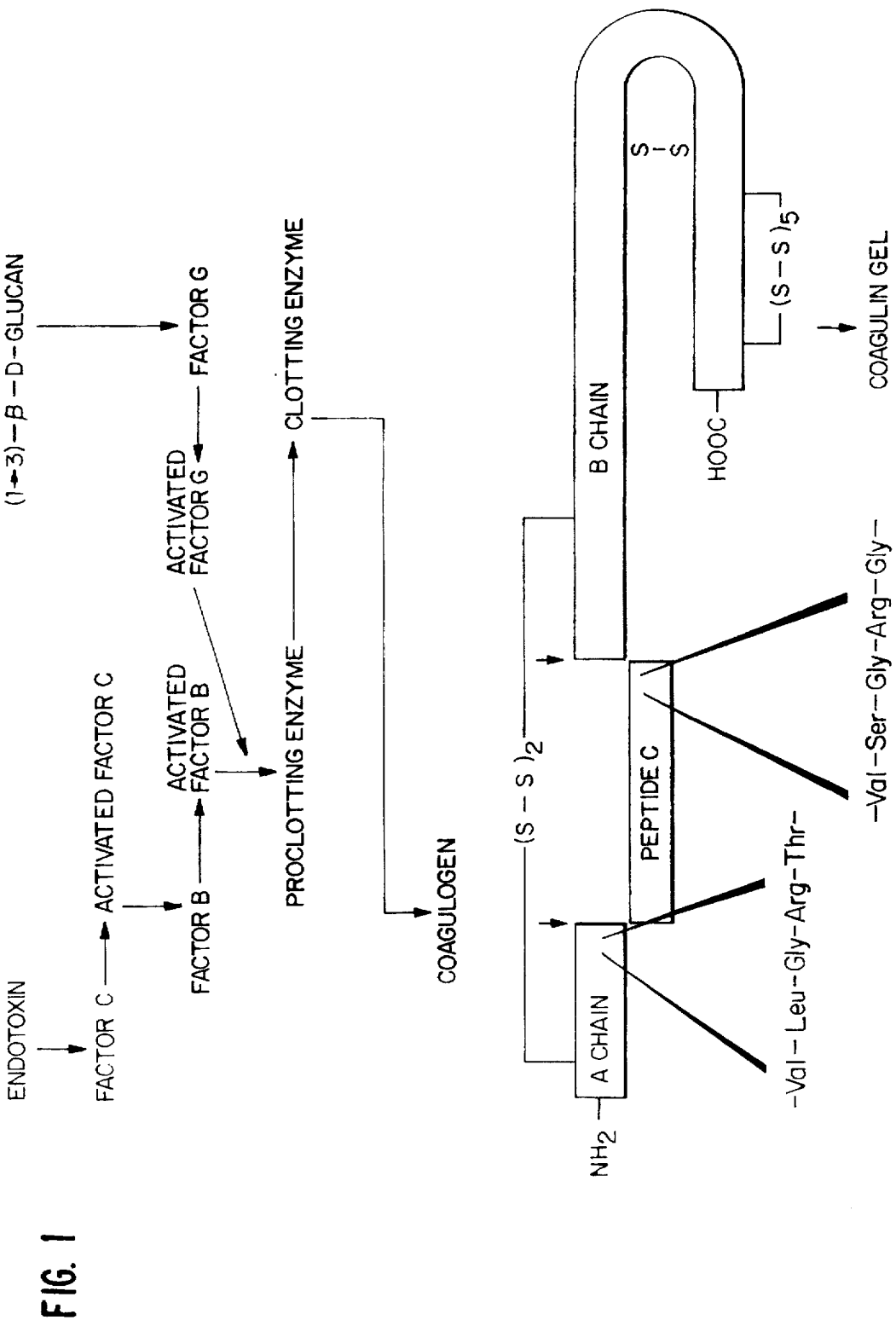
FIG. 1 is a diagram which illustrates the mechanism of the limulus reaction.

The alkylglucoside to be used in the present invention is not particularly restricted, so long as it consists of glucose to which an alkyl group is bound via a glycosidic linkage and has a function of inhibiting the activation of factor G. Although either an α-glucoside or a β-glucoside is usable herein, the latter is preferable to the former. Also, not only a common glucoside wherein an alkyl group is bound to glucose via an oxygen atom (i.e., an O-glucoside) but also a thioglucoside wherein an alkyl group is bound to glucose via a sulfur atom (i.e., an S-glucoside) is usable herein. Further those wherein an alkyl group is bound to glucose via, for example, selenium (Se) or tellurium (Te) may be used. The number of carbon atoms in the alkyl group to be bound to glucose is not particularly restricted, so long as the alkylglucoside is soluble or dispersible in water. In general, the carbon atom number preferably ranges from about 1 to 30, still preferably from about 6 to 12. The alkylglucoside of the present invention furthermore involves oligoglycosides or polyglycosides in which other saccharides are further bound to glucose, so long as the reducing end thereof is an alkylglucoside. Examples of such oligoglycosides or polyglycosides include polyglycosides having a definite number of (1→3)-β-D-glucoside structural units bound to each other, which are known as a factor G activation inhibitor (WO90/02951). In particular, preferred are n-octyl-β-D-glucoside, n-heptyl-β-D-glucoside, n-dodecyl-β-D-glucoside, n-octyl-β-D-thioglucoside and n-heptyl-β-D-thioglucoside, since they are easily available.

Examples of the limulus amebocyte lysate reagent to be used in the present invention (hereinafter sometimes referred to simply as the lysate reagent) include, hemocyte extracts prepared from the hemolymph of a horseshoe crab such as *Limulus polyphemus, Tachypleus tridentatus, Tachypleus gigas*, and *Carcinoscorpius rotundicauda* in a conventional manner [cf. for example, J. Biochem., 80, 1011–1021 (1976)]. To these extracts may be added, if necessary, divalent metal salts, for example, hydrohalogenic acid salts, such as chlorides, or sulfates, of alkaline earth metals such as magnesium, calcium and strontium, substrates of the clotting enzyme, for example, synthetic substrates such as the above-mentioned Boc-Leu-Gly-Arg-pNA, and pH adjusting reagent, for example, a buffer solution such as Tris hydrochloride buffer. Further, commercially available lysate reagents may be used therefor. Such a lysate reagent may be in the form of either liquid, powder or solid.

In order to achieve the object of the present invention, there may be employed: (A) a method comprising using a lysate reagent, to which an alkylglucoside has been added to thereby inactivate a component participating in the factor G system reaction (hereinafter sometimes referred to as a "alkylglucoside-containing lysate reagent"), in an assay; (B) a method comprising adding an alkylglucoside to a specimen and assaying this alkylglucoside-containing specimen using a common lysate reagent to thereby inactivate the component in the lysate reagent which participates in the factor G system reaction; or a method which is a combination of the methods (A) with (B), namely, an alkylglucoside is added to both the lysate reagent and the specimen.

Though the amount of the alkylglucoside required for completely inactivating the factor G system reaction in the lysate reagent depends on the type of the lysate reagent, one skilled in the art would easily determine the appropriate amount by, for example, the following method.

Under ice-cooling, an alkylglucoside (free from Et) is added in various amounts to a definite amount of the lysate reagent. Then a definite amount of β-glucan (free from Et) sufficient for the activation of the lysate reagent is added thereto under usual assay conditions, followed by the reaction under the conditions usually employed in the assay using the lysate reagent. Thus the amount of the alkylglucoside capable of completely inhibiting the activation of the lysate reagent by β-glucan is determined under the above-mentioned conditions.

Based on the required amount of the alkylglucoside thus determined, it is possible to determine the amount of the alkylglucoside for achieving the activity of the factor C system reaction giving an assay sensitivity suitable for the Et concentration in a specimen. The alkylglucoside is usually used in an amount of 0.05 to 10% w/v based on the lysate reagent.

The following methods (1) to (9) show examples of the way to bring the alkylglucoside into contact with the lysate reagent and/or the specimen for Et assay.

(1) A method which comprises adding an alkylglucoside to a limulus amebocyte in the process of extraction to give an alkylglucoside-containing lysate reagent.

(2) A method which comprises adding an alkylglucoside to an extracted lysate reagent to give an alkylglucoside-containing lysate reagent.

(3) A method which comprises dissolving a lyophilized lysate reagent in an alkylglucoside-containing solution to give an alkylglucoside-containing lysate reagent.

(4) A method which comprises dissolving a lyophilized lysate reagent in an appropriate solvent, adding an alkylglucoside to the resulting solution to give an alkylglucoside-containing lysate reagent.

(5) A method which comprises dissolving in an appropriate solution, a lysate reagent prepared by adding an alkylglucoside to a limulus amebocyte in the process of extraction, or a lysate reagent prepared by lyophilizing a lysate reagent to which a required amount of the alkylglucoside has been added, to give an alkylglucoside-containing lysate reagent.

(6) A method which comprises dissolving a lyophilized product containing a lysate reagent and a synthetic substrate in an alkylglucoside-containing solution or dissolving them in an appropriate solution and adding the alkylglucoside to the resulting solution.

(7) A method which comprises adding a required amount of an alkylglucoside to a mixture of a lysate reagent and a synthetic substrate, lyophilizing the mixture to give a lysate reagent and dissolving the reagent in an appropriate solution.

(8) A method which comprises adding a required amount of an alkylglucoside to a specimen.

(9) A method which comprises adding a specimen to a lysate reagent and then immediately thereafter adding an alkylglucoside thereto.

In the method for assaying Et according to the present invention, the alkylglucoside can be used in an arbitrary manner, so long as the factor C system reaction in the lysate reagent can give a sensitivity suitable for the purpose and within the appropriate assay range so as to enable the quantitative or qualitative determination of Et.

The solution to be used for dissolving lyophilized preparation in the above methods (3), (4), (5), (6) and (7) is an appropriate buffer capable of stably maintaining components in the lysate reagent involved in the factor C system reaction and maintaining an optimum pH range (pH 7.0 to 8.5) for a reaction of factor C with endotoxin. Examples of the solution include water and a buffer solution capable of maintaining the above pH range which contains a buffer agent such as Tris(hydroxymethyl)aminomethane, Tris(hydroxymethyl)aminomethanemaleate, 1,4-piperazinediethanesulfonate, morpholinopropanesulfonate, N-2-hydroxyethylpiperazine-N'-2-ethanesulfonate, triethanolamine, imidazole and Tris(hydroxymethyl)imidazole. The alkylglucoside-containing solution used in the above methods (3) and (6) is prepared by adding a necessary amount of an alkylglucoside to the above-described solution.

To assay Et using the assay reagent of the present invention, the activity of the clotting enzyme formed by the cascade reaction as shown in FIG. 1 may be determined by a known method.

In order to determine the amidase activity of the clotting enzyme, the above-mentioned synthetic peptide substrate having a chromogenic residue or those having the similar amino acid sequence except that the carboxyl group of the amino acid at the C-terminal is substituted not with the above-mentioned chromogenic residue but with a known fluorescent residue, luminescent residue or ammonia via an amide bond may be used as a substrate. The amidase activity can be determined by measuring the reaction product formed through the action of the clotting enzyme on the synthetic substrate. As mentioned more specifically below, the above-mentioned synthetic peptide substrate is added to a reaction system containing the assay reagent of the present invention and Et, and the colorant, fluorescent, luminescent substance or ammonia formed by the reaction (the cascade reaction followed by, if necessary, the conversion of the resulting product into, for example, another colorant) is measured by, for example, a spectrophotometer, a fluorophotometer, a chemiluminescence meter or an ammonia-detecting electrode (refer to JP-A-62-148860).

To determine the protease activity of the clotting enzyme, the gelation, i.e., the formation of a coagulin gel caused via the action of the clotting enzyme on the coagulogen (substrate) contained in, or separately added to, the assay reagent of the present invention may be measured by using an appropriate instrument (for example, a turbidimeter or a viscometer) or by judging with the naked eye.

Upon the practice of the present invention, the above-mentioned cascade reaction can be activated more effectively by divalent metal salt. Examples of such a divalent metal salt include hydrohalogenic acid salts (for example, chlorides, etc.) or sulfates of alkaline earth metals such as magnesium, calcium and strontium.

The above-mentioned metal salt may be separately added to the reagent of the present invention at the step of the limulus reaction. However it is usually preferable that the above-mentioned divalent metal salt is added to the lysate reagent which is then solidified by a dry treatment without heating (for example, lyophilization). The reagent for determining the above-mentioned amidase activity preferably contains not only the divalent metal salt but also the above-mentioned synthetic peptide substrate. This reagent may be subjected to a dry treatment. The divalent metal salt and the synthetic peptide substrate are used in an amount of 0.1 to 200 mM and 0.1 to 2 mM, respectively, in the reaction mixture.

The endotoxin assay according to the present invention can be carried out more easily and rapidly by using a kit comprising the above-described reagents. The kit of the present invention comprises the lysate reagent and the alkylglucoside-containing reagent. The alkylglucoside-containing reagent may further comprise not only water but also a buffer agent as described above. Specific example of the kit includes: (1) lyophilized lysate reagent and a solution for dissolving it in; (2) lyophilized alkylglucoside and a solution for dissolving it in; (3) lyophilized standard endotoxin and a solution for dissolving it in; and (4) reagents for synthetic chromogenic substrate method including distilled water for blank test.

The specimen to be subjected to the Et assay in accordance with the present invention is not substantially restricted, so long as it is needed to assay Et contained therein or to examine the presence of Et therein. Examples of the specimen include biological samples, drugs and water to be used in medical field.

The factor G activation inhibitor composition according to the present invention comprises an alkylglucoside as an active ingredient capable of inhibiting activation of factor G in limulus amebocyte by (1→3)-β-D-glucan and, water or a buffer agent free from Et.

The present invention has an economical advantage that a reagent for Et-specific assay can be easily produced simply by combining a lysate reagent with an alkylglucoside. Further, it is useful particularly in the examination of a clinical specimen which is suspected of infectious diseases or sepsis and the presence of Et in which is not clearly known. Thus it has an advantage that an infectious disease caused by gram negative bacteria (endotoxemia) can be accurately diagnosed.

To further illustrate the present invention in greater detail, the following Examples will be given, but are not to be understood to limit the scope of the present invention.

EXAMPLE 1

Addition of n-octyl-β-D-glucoside (glucopyranoside) to lysate reagent

1) A 1.0 l portion of the hemolymph of *T. tridentatus* was centrifuged at 1,500 rpm for 10 minutes at 4° C. To about 21 g of the precipitate (amebocyte) thus formed was added 210 ml of a 0.02M Tris hydrochloride buffer solution (pH 8.0). Then the mixture was uniformly ground with a homogenizer (Polytron R PT10$^R$, a trade name of a product manufactured by Kinematica), extracted and centrifuged under cooling at 10,000×G for 30 minutes. Thus 190 ml of a supernatant (a lysate reagent) was obtained.

To 0.04 ml of this lysate reagent were added 0.04 ml of a 0.5M Tris hydrochloride/0.4M magnesium sulfate buffer solution (pH 8.0) containing from 0.1 to 1.6 mg of a nonionic surfactant, n-octyl-β-D-glucoside respectively, and 0.02 ml of 4.0 mM Boc-Leu-Gly-Arg-pNA. Thus n-octyl-β-D-glucoside-containing lysate reagents (the invention products.) were obtained. To 0.04 ml of another lysate reagent were added 0.04 ml of a 0.5M Tris hydrochloride/0.4M magnesium sulfate buffer solution (pH 8.0) containing no n-octyl-β-D-glucoside and 0.02 ml of 4.0 mM Boc-Leu-Gly-Arg-pNA. A 0.1 ml portion each of distilled water (hereinafter referred to simply as DW; employed as a blank) and β-glucan (500 ng/ml) prepared by the following method were separately added to these lysate reagents as a specimen. Each mixture thus obtained was incubated at 37° C. for 30 minutes. Then the paranitroaniline thus formed was subjected to diazocoupling by successively adding 0.5 ml portions of 0.04 % sodium nitrite (a 0.48M hydrochloric acid solution), 0.3 % ammonium sulfamate and 0.07% N-1-naphthylethylenediamine dihydrochloride. The absorbance of the mixture was measured at 545 nm and the difference from the specimen's absorbance to the blank one was shown as the reactivity in Table 1. (In the following Examples and Tables, Δ means a difference from the specimen's absorbance to the blank one.)

TABLE 1

| n-Octyl-β-D-glucoside (mg) | Reactivity (ΔA 545 nm/30 min) |
|---|---|
| 0 | >1.5 |
| 0.1 | 0.503 |
| 0.2 | 0.148 |
| 0.4 | 0.000 |
| 0.8 | 0.000 |
| 1.6 | 0.000 |

As Table 1 clearly shows, the activation of factor G in the lysate reagent by β-glucan can be completely inhibited by adding 0.4 mg or more of n-octyl-β-D-glucoside to 0.04 ml of the lysate reagent.

Figure 2:
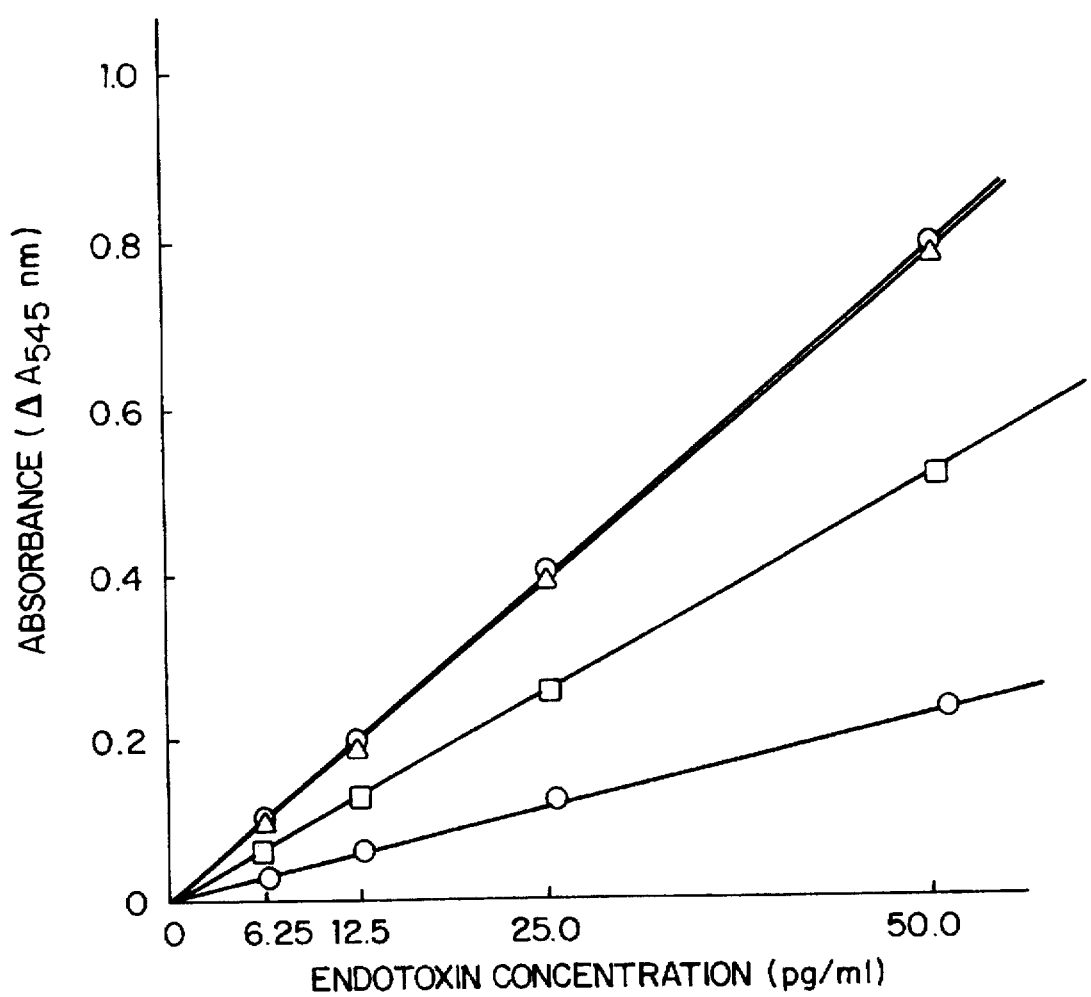
FIG. 2 is a result of Example 1-2) which shows calibration curves prepared by plotting absorbance against an endotoxin concentration in the case of adding various amounts of n-octyl-β-D-glucoside (-○-: not added, -△-: 0.4 mg, -□-: 0.8 mg and -●-: 1.6 mg).

2) To 0.04 ml of the lysate reagent were added 0.04 ml of a 0.5M Tris hydrochloride/0.4M magnesium sulfate buffer solution (pH 8.0) containing from 0.4 to 1.6 mg of n-octyl-β-D-glucoside respectively, which completely inhibited the factor G system reaction in the lysate reagent by β-glucan as shown in the above 1), and 0.02 ml of 4.0 mM Boc-Leu-Gly-Arg-pNA. Thus, lysate reagents containing n-octyl-β-D-glucoside were obtained. To 0.04 ml of another lysate reagent were added, 0.04 ml of a 0.5M Tris hydrochloride/ 0.4 M magnesium sulfate buffer solution (pH 8.0) containing no n-octyl-β-D-glucoside and 0.02 ml of 4.0 mM Boc-Leu-Gly-Arg-pNA. A 0.1 ml portion each of DW (blank), Et derived from *Escherichia coli* 0111:B4 strain (Westphal type, commercially available from Sigma, 6.25, 12.5, 25.0, 50.0 pg/ml) were separately added to these lysate reagents as a specimen. Then these mixtures were incubated in the same manner as in 1) to thereby prepare Et calibration curves. FIG. 2 shows the results. As FIG. 2 clearly shows, the reactivity to Et is lowered with an increase in the amount of the added n-octyl-β-D-glucoside (referred to as O.G. in FIG. 2). Based on these calibration curves, the amount of n-octyl-β-D-glucoside capable of giving a reactivity of the factor C system reaction in a lysate reagent for achieving an assay sensitivity corresponding to the Et concentration in a specimen can be arbitrarily selected.

These results indicate that Et in a specimen can be specifically assayed without being affected by β-glucan by using a limulus test reagent prepared by adding n-octyl-β-D-glucoside to a common lysate reagent.

Method for the preparation of β-glucan

In accordance with a method described in PCT International Publication WO90/02951, 1 g of curdlan (commercially available from Wako Pure Chemical Industries, Ltd.) was suspended in about 100 ml of a 5 mM aqueous solution of NaOH. Then it was degraded by sonicating with Sonicator™ (Ohtake Seisaku-sho, Model 5202PZT, Tokyo) at 20 kHz and 80 W for 12 minutes under ice-cooling. The solution thus treated was adjusted to a 0.3M aqueous solution using a 5M aqueous solution of NaOH. Then it was fractionated by gel permeation chromatography (GPC column: two of TSK gel G3000PW$_{XL}$ column and one of G2500PW$_{XL}$ column, mobile phase: 0.3M aqueous solution of NaOH, flow rate: 0.5 ml/min). A fraction corresponding to a molecular weight of 216,000 was collected by repeating the chromatography to thereby obtain a purified preparation of GPC fraction (a β-glucan preparation).

The β-glucan employed in the following Examples was one prepared by the same method as described above.

EXAMPLE 2

Addition of n-octyl-β-D-glucoside (glucopyranoside) in the process of extraction of limulus amebocyte A 1.0 l portion of the hemolymph of *T. tridentatus* was centrifuged at 4° C. at 1,500 rpm for 10 minutes. To about 21 g of the precipitate (amebocyte) thus formed was added 210 ml of a 0.02M Tris hydrochloride buffer solution (pH 8.0) containing 2.0 g of n-octyl-β-D-glucoside. Then the mixture was uniformly ground with Polytron R PT10$^R$, extracted and centrifuged under cooling at 10,000×G for 30 minutes. Thus 190 ml of a supernatant (a lysate reagent containing n-octyl-β-D-glucoside) was obtained.

To 0.04 ml portions of this lysate reagent containing n-octyl-β-D-glucoside (an invention example) and another lysate reagent prepared by adding no n-octyl-β-D-glucoside in the above-mentioned procedure (a comparative example) were added 0.01 ml of a 2M Tris hydrochloride buffer solution (pH 8.0), 0.03 ml of 0.4M magnesium chloride and 0.02 ml of 3.0 mM Boc-Leu-Gly-Arg-pNA. Further, 0.1 ml portions of DW (blank), Et and β-glucan were separately added thereto as a specimen. Furthermore, 0.05 ml portions of Et and β-glucan, each at a concentration twice as high as the above one, were simultaneously added as another specimen. These mixtures were reacted at 37° C. for 30 minutes. After stopping the reaction by adding 0.4 ml of 0.8M acetic acid, the absorbance of each reaction mixture was measured at 405 nm to thereby determine the amount of paranitroaniline thus formed. Thus the reactivity was compared. Table 2 shows the results. As Table 2 shows, Et can be specifically assayed without being affected by β-glucan by using the n-octyl-β-D-glucoside-containing lysate reagent which is prepared by adding n-octyl-β-D-glucoside in the process of extracting a lysate reagent from limulus hemolymph. In other words, it has been proved that in the assay of the present invention, the factor G system reaction is substantially suppressed without inhibiting the factor C system reaction.

TABLE 2

| Specimen | Reactivity (ΔA 405 nm/30 min) | |
|---|---|---|
| | Invention | Comparison |
| Et* | 0.319 | 0.351 |
| β-glucan** | 0.000 | 0.191 |
| Et + β-glucan | 0.319 | 0.541 |

*Et concentration: 3.0 pg/0.1 ml specimen.
**β-glucan concentration: 5.0 pg/0.1 ml specimen.

EXAMPLE 3

Addition of n-octyl-β-D-thioglucoside (thioglucopyranoside) at the step of dissolution of lyophilized lysate reagent One vial of "Pyrotel" (a lyophilized lysate reagent prepared by extraction from *L. polyphemus*; a limulus test reagent for gelation method; manufactured by Cape Cod and commercially available from Seikagaku Corporation) was dissolved in 5.0 ml of an aqueous solution containing 55 mg of n-octyl-β-D-thioglucoside (an invention example). Separately, another vial of the lyophilized product was dissolved in 5.0 ml of DW containing no n-octyl-β-D-thioglucoside (a comparative example). A 0.1 ml portion each of these lysate reagents was pipetted into reaction tubes. Further, 0.1 ml portions of DW (blank), Et and β-glucan were separately added thereto as a specimen. Furthermore, 0.05 ml portions of Et and β-glucan, each at a concentration twice as high as the above one, were simultaneously added as another specimen. After gently mixing, each reaction mixture was set to an analysis module for exclusive use of a time-turbidimeter "Toxinometer ET-201" (commercially available from Wako Pure Chemical Industries, Ltd.) at 37° C. for 60 minutes and the gelation time (Tg) was recorded to thereby examine the reactivity of the assay reagent of the present invention. Table 3 shows the results. These results indicate that Et can be specifically assayed without being affected by β-glucan by adding n-octyl-β-D-thioglucoside to a commercially available lyophilized lysate reagent (a limulus test reagent for gelation method) prior to the addition of a specimen.

TABLE 3

| Specimen | Reactivity (Tg; min) | |
|---|---|---|
| | Invention | Comparison |
| DW (blank) | >60 | >60 |
| Et* | 33.2 | 29.2 |
| β-glucan** | >60 | 31.8 |
| Et + β-glucan | 33.0 | 18.8 |

*Et concentration: 2.0 pg/0.1 ml specimen.
**β-glucan concentration: 40.0 pg/0.1 ml specimen.

EXAMPLE 4

Addition of n-decyl-β-D-glucoside (glucopyranoside) at the step of dissolution of lyophilized preparation of lysate reagent and synthetic substrate One vial of "Toxicolor System LS-200 set" (a lyophilized preparation of lysate reagent extracted and prepared from *T. tridentatus* with, for example, Boc-Leu-Gly-Arg-pNA; a limulus test reagent for chromogenic synthetic substrate method; commercially available from Seikagaku Corporation) was dissolved in 2.8 ml of a 0.2M Tris hydrochloride buffer solution (pH 8.0) containing 28 mg of n-decyl-β-D-glucoside to thereby give an assay reagent of the present invention. Separately, another vial of the lyophilized preparation was dissolved in 2.8 ml of a 0.2M Tris hydrochloride buffer solution (pH 8.0) containing no n-decyl-β-D-glucoside to thereby give a comparative reagent. To 0.1 ml portions of these lysate reagents were separately added 0.1 ml portions of DW (blank), Et and β-glucan as a specimen. Furthermore, 0.05 ml portions of Et and β-glucan, each at a concentration twice as high as the above one, were simultaneously added thereto as another specimen. These mixtures were reacted in the same manner as in Example 1-1) to thereby examine the reactivity of the assay reagent of the present invention. Table 4 shows the results.

TABLE 4

| Specimen | Reactivity (ΔA 545 nm/30 min) | |
|---|---|---|
| | Invention | Comparison |
| Et* | 0.847 | 0.882 |
| β-glucan** | 0.000 | >1.5 |
| Et + β-glucan | 0.847 | >1.5 |

*Et concentration: 5.0 pg/0.1 ml specimen.
**β-glucan concentration: 50.0 ng/0.1 ml specimen.

These results indicate that Et can be specifically assayed without being affected by β-glucan by adding n-decyl-β-D-glucoside to a lyophilized preparation of a commercially available limulus test reagent for the chromogenic synthetic substrate method.

EXAMPLE 5

Use of lyophilized lysate reagent prepared by adding n-octyl-β-D-glucoside to limulus amebocyte in the process of extraction Similar to the above Example 2, 2.0 ml of an n-octyl-β-D-glucoside-containing lysate reagent, which had been prepared by adding n-octyl-β-D-glucoside in the process of extraction, and 0.4 ml of 0.4M magnesium chloride were mixed together and lyophilized to thereby give a reagent for Et-specific assay according to the present invention. Similarly, 2.0 ml of a lysate reagent containing no n-octyl-β-D-glucoside, which had been prepared in the same manner as the one of Example 1-1), and 0.4 ml of 0.4M magnesium chloride were mixed together and lyophilized to thereby give a comparative assay reagent. Each of these lyophilized products was dissolved in 2.0 ml of DW. To 0.1 ml of the resulting solution, 0.1 ml portions of DW (blank), Et and β-glucan were separately added as a specimen. After gently mixing, each reaction mixture was allowed to stand at 37° C. for 60 minutes. Then it was turned upside down and the formation of a gel was judged with the naked eye to thereby examine the reactivity of the assay reagent of the present invention. Table 5 shows the results in which "+" means that a gel was formed while "-" means that no gel was formed.

TABLE 5

| Specimen | Reactivity | |
|---|---|---|
| | Invention | Comparison |
| DW (blank) | – | – |
| Et* | + | + |
| β-Glucan** | – | + |

*Et concentration: 4.0 pg/0.1 ml specimen.
**β-glucan concentration: 40.0 ng/0.1 ml specimen.

These results indicate that Et can be specifically assayed without being affected by β-glucan by lyophilizing an n-octyl-β-D-glucoside-containing lysate reagent which had been prepared by adding n-octyl-β-D-glucoside in the process of extraction.

EXAMPLE 6

Use of reagent for Et-specific assay prepared by mixing lysate reagent, synthetic substrate and n-octyl-β-D-glucoside followed by lyophilization After mixing 2.0 ml of the lysate reagent containing no n-octyl-β-D-glucoside obtained in the above Example 1-1), 0.9 ml of a 3.4 mM chromogenic synthetic substrate (Boc-Leu-Gly-Arg-pNA), 1.0 ml of 0.8M magnesium sulfate and 0.5 ml of an aqueous solution containing 25 mg of n-octyl-β-D-glucoside, the mixture was lyophilized to give a reagent for Et-specific assay of the present invention. Also, the above-mentioned procedure was repeated except for substituting the aqueous solution of n-octyl-β-D-glucoside with 0.5 ml of DW to thereby give a comparative assay reagent. Each of these lyophilized products was dissolved in 5.0 ml of a 0.2M Tris hydrochloride buffer solution (pH 8.0). To 0.1 ml portions of these solutions, 0.1 ml portions of DW (blank), Et and β-glucan were separately added as a specimen. Furthermore, 0.05 ml portions of Et and β-glucan, each at a concentration twice as high as the above one, were simultaneously added thereto as another specimen. These mixtures were reacted in the same manner as in Example 1-1) to thereby examine the reactivity of the assay reagent of the present invention. Table 6 shows the results.

TABLE 6

| Specimen | Reactivity (ΔA 545 nm/30 min) | |
|---|---|---|
| | Invention | Comparison |
| Et* | 0.663 | 0.702 |
| β-glucan** | 0.000 | >1.5 |
| Et + β-glucan | 0.663 | >1.5 |

*Et concentration: 4.0 pg/0.1 ml specimen.
**β-glucan concentration: 40.0 ng/0.1 ml specimen.

These results indicate that Et can be specifically assayed without being affected by β-glucan by mixing a lysate reagent, a synthetic substrate and n-octyl-β-D-glucoside followed by lyophilization.

EXAMPLE 7

Addition of n-octyl-β-D-glucoside to specimen prior to assay

As a specimen, 0.05 ml portions of DW (blank), Et and β-glucan and an equivalent volume mixture of Et and β-glucan, each at a concentration twice as high as the above one, were prepared. Then 0.05 ml of an aqueous solution containing 1.2 mg of n-octyl-β-D-glucoside was added to each of them. After further adding 0.1 ml of "Toxicolor System LS-200 Set" dissolved in 2.8 ml of a 0.2M Tris hydrochloride buffer solution (pH 8.0), the resulting mixture was reacted in the same manner as in the above Example 1-1). Also, the above procedure was repeated except for substituting the aqueous solution of n-octyl-β-D-glucoside with DW to thereby compare the reactivity. Table 7 shows the results.

TABLE 7

| Specimen | Reactivity (ΔA 545 nm/30 min) | |
|---|---|---|
| | Invention | Comparison |
| Et* | 0.874 | 0.902 |
| β-glucan** | 0.000 | >1.5 |
| Et + β-glucan | 0.875 | >1.5 |

*Et concentration: 5.0 pg/0.05 ml specimen.
**β-glucan concentration: 30.0 ng/0.05 ml specimen.

These results indicate that Et can be specifically assayed without being affected by β-glucan by adding n-octyl-β-D-glucoside to a specimen prior to assay.

EXAMPLE 8

Addition of specimen to lysate reagent immediately followed by the addition of n-octyl-β-D-glucoside One vial of "Pyrotel" was dissolved in 5.0 ml of DW and 0.1 ml portions of the solution thus obtained were pipetted into test tubes under ice-cooling. Then 0.05 ml portions of DW (blank), Et and β-glucan were separately added thereto as a specimen. Immediately thereafter, 0.05 ml of an aqueous solution containing 1.3 mg of n-octyl-β-D-glucoside was added to each test tube. After gently mixing and allowing to stand at 37° C. for 60 minutes, the formation of a gel was judged in the same manner as in Example 5. Also, the above procedure was repeated except for substituting the aqueous solution of n-octyl-β-D-glucoside with the same amount of DW to thereby compare the reactivity. Table 8 shows the results.

TABLE 8

| Specimen | Reactivity | |
|---|---|---|
| | Invention | Comparison |
| DW (blank) | – | – |
| Et* | + | + |
| β-glucan** | – | + |

*Et concentration: 2.0 pg/0.05 ml specimen.
**β-glucan concentration: 20.0 ng/0.05 ml specimen.

These results indicate that Et can be specifically assayed without being affected by β-glucan by adding a specimen to a lysate reagent and then immediately adding n-octyl-β-D-glucoside thereto.

EXAMPLE 9

Platelet rich plasma collected from patients who were suspected of the complication of sepsis was treated with perchloric acid according to the method described in U.S.

Pat. No. 4,495,294 and neutralized to serve as a specimen. Et in a 0.1 ml portion thereof was assayed in accordance with the present invention by the same method as in Example 2. Further, the specimen was also cultured according to the usual method to detect microbial infection. As a result, it was confirmed that the number of E. coli colonies were detected in conformity with the quantitative reactivity of Et.

This test was repeated in accordance with the methods of Examples 3 to 8. As a result, effectiveness of the reagents or the methods of the present invention has been confirmed.

COMPARATIVE EXAMPLE

To 0.04 ml of the lysate reagent obtained in Example 1-1) were added 0.04 ml of 0.5M Tris-hydrochloride-0.4M magnesium sulfate buffer (pH 8.0) containing 0.5 mg of n-octyl-β-D-glucoside or a nonionic surfactant recited in Table 9 and 0.02 ml of 4.0 mM Boc-Leu-Gly-Arg-pNA. Separately, 0.04 ml of 0.5M Tris-hydrochloride-0.4M magnesium sulfate buffer (pH 8.0) containing no nonionic surfactant and 0.02 ml of 4.0 mM Boc-Leu-Gly-Arg-pNA were added to 0.04 ml of the lysate reagent (control reagent). A 0.1 ml portion of DW (blank), *Escherichia coli* 0111:B4 strain-derived Et (25 pg/ml) or β-glucan (50 pg/ml) was respectively added to the reagent and the control reagent as prepared above as a specimen. After the reaction was carried out in the same manner as in Example 1-1), the absorbance was measured at 545 nm and the difference from the specimen's absorbance to the blank one was shown as the reactivity. The reactivity of the surfactant-containing reagent to Et or β-glucan was determined as relative activity to control reactivity.

The results are shown in Table 9.

TABLE 9

| Specimen | Relative activity (%) | | | | | | |
|---|---|---|---|---|---|---|---|
| | Control | n-octyl-β-D-glucoside | Tween-80 | Tween-20 | Span-20 | Briji-92 | Triton X-100 |
| Et | 100 | 100.0 | 15.5 | 13.2 | 11.9 | 10.1 | 2.2 |
| β-glucan | 100 | 0 | 11.2 | 12.0 | 23.4 | 12.4 | 34.2 |

Note:
n-octyl-β-D-glucoside available from Dojin Kagaku Kenkyusho
Tween-80 (trade name) available from Sigma Chemical Co.
Tween-20 (trade name) available from Wako Pure Chemical Industry., Co., Ltd.
Span-20 (trade name) available from Sigma Chemical Co.
Briji-92 (trade name) available from Sigma Chemical Co.
Trtion X-100 (trade name) available from Aldrich Chemical Company, Inc.

As shown in Table 9, Et can be specifically assayed using the reagent containing n-octyl-β-D-glucoside as compared with the nonionic surfactants.

While the invention has been described in detail and with reference to specific examples thereof, it will be apparent to one skilled in the art that various changes and modifications can be made therein without departing from the spirit and scope thereof.

What is claimed is:

1. A reagent for endotoxin-specific assay which comprises a limulus amebocyte lysate reagent and an alkylglucoside.

2. The reagent for endotoxin-specific assay according to claim 1, wherein said alkylglucoside is contained in an amount effective for inhibiting activation of factor G existing in said limulus amebocyte lysate reagent.

3. The reagent for endotoxin-specific assay according to claim 1, wherein an alkyl group contained in the alkylglucoside has from 1 to 30 carbon atoms.

4. The reagent for endotoxin-specific assay according to claim 1, wherein, in said alkylglucoside, glucose or glucose of a reducing end of a glucoside moiety is bound to an alkyl group via a glycosidic linkage.

5. The reagent for endotoxin-specific assay according to claim 4, wherein said alkylglucoside is an alkyl-O-β-D-glucoside or an alkyl-S-β-D-glucoside.

6. The reagent for endotoxin-specific assay according to claim 4, wherein said alkylglucoside is selected from the group consisting of n-octyl-β-D-glucoside, n-heptyl-β-D-glucoside, n-dodecyl-β-D-glucoside, n-octyl-β-D-thioglucoside and n-heptyl-β-D-thioglucoside.

7. The reagent for endotoxin-specific assay according to claim 1, wherein said alkylglucoside is soluble or dispersible in water.

8. A method of assaying for endotoxin in a specimen using a limulus amebocyte lysate reagent, comprising the steps of:
   (a) adding an alkylglucoside to the limulus amebocyte lysate reagent and/or the specimen, and
   (b) assaying for endotoxin in the specimen.

9. The method of specifically assaying endotoxin according to claim 8, wherein the alkylglucoside is added in an amount effective for inhibiting activation of factor G existing in the limulus amebocyte lysate reagent.

10. The method of specifically assaying endotoxin according to claim 8, wherein, in said alkylglucoside, glucose or glucose of a reducing end of a glucoside moiety is bound to an alkyl group via a glycosidic linkage.

11. A kit for endotoxin-specific assay which comprises a limulus amebocyte lysate reagent and a reagent containing an alkylglucoside.

12. The kit according to claim 11, wherein said reagent containing alkylglucoside further contains a buffer agent.

13. The kit according to claim 11, which further comprises a reagent containing a substrate for clotting enzyme.

14. The kit according to claim 13, wherein said substrate is a coagulogen or a synthetic peptide substrate.

15. The kit for endotoxin-specific assay according to claim 11, wherein, in said alkylglucoside, glucose or glucose of a reducing end of a glucoside moiety is bound to an alkyl group via a glycosidic linkage.

16. A factor G activation inhibitor composition which comprises an alkylglucoside as an active ingredient capable of inhibiting the activation of factor G existing in limulus amebocyte by (1→3)-β-D-glucan and, water or a buffer agent free from endotoxin.

17. The factor G activation inhibitor composition according to claim 16, wherein, in said alkylglucoside, glucose or glucose of a reducing end of a glucoside moiety is bound to an alkyl group via a glycosidic linkage.

18. A method for inhibiting activation of factor G existing in a limulus amebocyte lysate reagent comprising the step of adding an alkylglucoside to the limulus amebocyte lysate reagent.

19. The method for inhibiting activation of factor G according to claim 18, wherein, in said alkylglycoside, glucose or glucose of a reducing end of a glucoside moiety is bound to an alkyl group via a glycosidic linkage.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Val Leu Gly Arg
      1

( 2 ) INFORMATION FOR SEQ ID NO:2:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

Ile Glu Gly Arg
      1

( 2 ) INFORMATION FOR SEQ ID NO:3:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Val Ser Gly Arg
      1